(12) United States Patent
Jackstell et al.

(10) Patent No.: US 6,924,389 B2
(45) Date of Patent: Aug. 2, 2005

(54) METHOD FOR PRODUCING DIPHOSPHINES AND THE USE THEREOF

(75) Inventors: Ralf Jackstell, Wittenberg (DE); Holger Klein, Rockstock (DE); Matthias Beller, Rostock (DE); Klaus-Diether Wiese, Haltern (DE); Cornelia Borgmann, Recklinghausen (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/471,748
(22) PCT Filed: Mar. 19, 2002
(86) PCT No.: PCT/EP02/02989
§ 371 (c)(1),
(2), (4) Date: Sep. 25, 2003
(87) PCT Pub. No.: WO02/076996
PCT Pub. Date: Oct. 3, 2002

(65) Prior Publication Data
US 2004/0110979 A1 Jun. 10, 2004

(30) Foreign Application Priority Data
Mar. 26, 2001 (DE) .......................................... 101 14 868

(51) Int. Cl.$^7$ ............................... C07F 9/22; C07F 9/28
(52) U.S. Cl. ............................... 562/8; 564/15; 568/17; 568/14
(58) Field of Search ............................... 562/8; 564/15; 568/17, 14; 585/466, 26, 411, 436, 469

(56) References Cited

U.S. PATENT DOCUMENTS

| | | | | |
|---|---|---|---|---|
| 4,694,109 A | | 9/1987 | Devon et al. | |
| 5,510,554 A | * | 4/1996 | Regnat et al. | ............... 562/519 |
| 5,600,006 A | * | 2/1997 | Regnat et al. | ................ 568/16 |
| 5,767,317 A | * | 6/1998 | Kleiner et al. | ................ 568/14 |

FOREIGN PATENT DOCUMENTS

| | | |
|---|---|---|
| EP | 0 653 432 | 5/1995 |
| EP | 0 673 944 | 9/1995 |
| EP | 0 704 449 | 4/1996 |

OTHER PUBLICATIONS

Klein et al., Highly Selective Catalyst Syatems for the Hydroformylation of Internal Olefins to Linear Aldehydes, Angew. Chem. Int. Ed., 2001, 40, No. 18, pp. 3408–3411.*
Klein H et al: "Highly selective catalyst systems for the hydroformylation of internal olefins to linear aldehydes" Angewandte Chemie, International Edition, vol. 40, No. 18, 17, pp. 3408–3411 Sep. 17, 2001.
Gillie A et al: "Mechanisms of 1, 1–Reductive Elimination from Palladium" Journal of the American Chemical Society, vol. 102, No. 15, pp. 4933–4941 1980.
Dani P et al: "Replacement of a Cyclometalated Terdentate Diamino Ligand by a Phosphorus Analogue, Isolation and Crystallographic Characterization of an Intermediate in Aryl C–H Bond Activation in Models of Dendrimer–Bound Organometallic Catalysts" Journal of the American Chemical Society, vol. 119, No. 46, pp. 11317–11318, 1997.
Yamamoto Y et al: "Preparation and characterization of palladium platinum and complexes bearing 1,8–bis [(diphenylphosphino) methyl]naphthalene" Journal of the Chemical Society, pp. 1773–1781, 2001
Goertz W et al: "Asymmetric Nickel–Catalyzed Hydrocyanation of Vinylarenes by Applying Homochiral Xantphos Ligands" Chemistry, A European Journal, vol. 7, No. 8, pp. 1614–1618 2001.
Goertz W et al: "Electronic effects in the nickel–catalysed hydrocyanation of styrene applying chelating phosphorous ligands with large bite angles" Journal of the Chemical Society, Dalton Transactions, pp. 2981–2988 1998.
Bentrude W G et al: "Free–radical chemistry of organophosphorus compound. IV. Polar, bond strength, and resonance effects of phosphoranyl radical formation" Journalof the American Chemical Society, vol. 95, No. 11, pp. 3625–3635 May 30, 1973.
Evleth E M et al: "p–Phenylenediphosphine and Related Compounds" Journal of Organic Chemistry, American Chemical Society, vol. 27, pp. 2192–2197, 1962.
Marinetti A et al: "New Chiral Dichlorophosphines and Their Use in the Synthesis of Phosphetane Oxides and Phosphinic Chlorides" Journal of Organic Chemistry, American Chemical Society, vol. 62, No. 2, pp. 297–301, Jan. 24, 1997.

(Continued)

Primary Examiner—Johann Richter
Assistant Examiner—Chukwuma Nwaonicha
(74) Attorney, Agent, or Firm—Oblon, Spivak, McClelland, Maier & Neustadt, P.C.

(57) ABSTRACT

Diphosphine of formula I $$R^1R^2P-H_2C-Ar-CH_2PR^1R^2 \quad (I)$$

are prepared by a process that comprises a) reacting a dimethyl compound of formula II $$H_3C-Ar-CH_3 \quad (II)$$

with a base and an N-substituted aminophosphorous halide to form bis(aminophosphinomethyl) compound of the formula III $$R^3R^4P-H_2C-Ar-CH_2-PR^3R^4 \quad (III)$$

b) reacting the compound of formula III with HCl to form bis(dichlorophosphinomethyl) compound of formula IV $$Cl_2P-H_2C-Ar-CH_2-PCl_2 \quad (IV)$$

and c) reacting the compound of formula IV with an organometallic reagent to give the product compound of formula I, wherein groups $R^1$ and $R^2$ are each, independently of one another, a substituted or unsubstituted aromatic, heteroaromatic or aliphatic hydrocarbon group and may have a covalent bond connecting them and Ar is a substituted or unsubstituted aromatic or heteroaromatic hydrocarbon group an $R^3$ and $R^4$ are each, independently of one another, an N-substituted alkylamino or arylamino group.

7 Claims, No Drawings

OTHER PUBLICATIONS

Reetz M T et al: "New non–$C_2$–symmetric phosphine–phosphonites as ligands in asymmetric metal catalysis" Tetrahedon: Asymmetry, vol. 10, No. 11, pp. 2129–2137 Jun. 4, 1999.

Van Doorn J A et al: "Reductive cleavage of the carbon–phosphorus bond with alkali metals. III Reactions of arylalkylphosphines" Recueil des Travaux Chimiques des Pays–Bas, vol. 111, No. 4, pp. 170–177, 1992.

Klein H et al: "Highly selective catalyst systems for the hydroformylation of internal olefins to internal aldehydes" Angewandte Chemie, International Edition, vol. 40, No. 18, Sep. 17, 2001 pp. 3408–3411, XP002203112 the whole document.

Gillie A et al: "Mechanisms of 1, 1–Reductive Elimination from Palladium" Journal of the American Chemical Society, vol. 102, No. 15, 1980, pp. 4933–4941, XP002203113 the whole document.

Dani P et al: "Replacement of a Cyclometalated Terdentate Diamino Ligand by a Phosphorus Analogue. Isolation and Crystallographic Characterisation of an Intermediate in Aryl C–H Bond Activation in Models of Dendrimer–Bound Organometallic Catalysts" Journal of the American Chemical Society, vol. 119, No. 46, 1997, pp. 11317–11318, XP00203114 the whole document.

Yamamoto Y et al: "Preparation and characterization of palladium platinum complexes bearing 1,8–bis (diphenylphosphino) methyl!naphtalene" Journal of the Chemical Society, Dalton Transactions, 2001, pp. 1773–1781, XP002203115 the whole document.

Goertz W et al: "Asymetric Nickel–Catalyzed Hydrocyanation of Vinylarenes by Applying Homochiral Xantphos Ligands" Chemistry, A European Journal, vol. 7, No. 8, 2001, pp. 1614–1618, XP002203116 Seite 1617, Synthese der Verbindung 1.

Goertz W et al: "Electronic effects in the nickel–catalysed hydrocyanation of styrene applying chelating phosphorous ligands with large bite angles" Journal of the Chemical Society, Dalton Transactions, 1998, pp. 2981–2988, XP002195283 Seite 2986, Herstellung des Ligands L2a.

Bentrude W G et al: "Free–radical chemistry of organophosphorus compound. IV. Polar, bond strength and resonance effects of phosphoranyl radical formation" Journal of the American Chemical Society, vol. 95, No. 11, May 30, 1973, pp. 3625–3635, XP002203117 p. 3634, col. 1, line 19–line 24.

Evleth E M et al: "P–Phenylenediphosphine and Related Compounds" Journal of Organic Chemistry, American Chemical Society, Easton, US, vol. 27, Jun. 1962, pp. 2192–2197, XP001021629 ISSN:0022–3263 Seite 2192, Reaktionsschema.

Marinetti A et al: "New Chiral Dichlorophosphines and Their Use in the Synthesis of Phosphetane Oxides and Phosphinic Chlorides" Journal of Organic Chemistry, American Chemical Society. Easton, US, vol. 62, No. 2, Jan 24, 1997, pp. 297–301, XP000640625 ISSN: 0022–3263 Seite300, Synthese von 5a.

Reetz M T et al: "New non–C2–symmetric phosphine–phosphonites as ligands in asymmetric metal catalysis" Tetrahedon: Asymmetry, vol. 10, No. 11, Jun. 4, 1999, pp. 2129–2137, XP004174097 ISSN: 0957–4166 Seite 2130, Schema 1; Seite 2134, Teil 4.5.

Van Doorn J A et al: "Reductive cleavage of the carbon–phosphorus bond with alkali metals. III Reactions of arylalkylphosphines" Recueil des Travaux Chimiques des Pays–Bas, vol. 111, No. 4, 1992, pp. 170–177, XP001084949 Seite 175, rechte, Spaite, 1. Absatz des Experimental.

* cited by examiner

METHOD FOR PRODUCING DIPHOSPHINES AND THE USE THEREOF

BACKGROUND OF THE INVENTION

1. Field of the Invention

The present invention relates to an improved process for preparing diphosphines such as bis(diarylphosphinomethyl) arenes.

2. Description of the Background

Phosphines have many applications in industry. They have industrial importance as antioxidants, metal extractants, flame retardant impregnants, stabilizers for olefins, starting materials for Wittig reagents and, in particular, as ligands for transition metal catalysts.

A review of the important homogeneous catalysts containing phosphine ligands may be found, for example, in B. Cornils, W. A. Herrmann, Applied Homogeneous Catalysis with Organometallic Compounds Vol. 1 & 2, VCH, Weinheim, 1996. Within the group of phosphines, chelating phosphines, in particular diphosphines, are of particular importance as ligands for metal complexes. This is due to the fact that diphosphines form more stable complexes with the appropriate central metal atom and therefore have a more lasting influence on its catalytic properties. Among the known chelating diphosphines, bis(diarylphosphinoalkyl)-1,1'-binaphthyls as constituents of carbonylation catalysts and telomerization catalysts are of industrial interest. EP 0 653 432, EP 0 673 944 and JP 7939059 describe the preparation of bis(diarylphosphinoalkyl)-1,1'-binaphthyls by reaction of 2,2'-dimethylbinaphthyls with a brominating agent to form 2,2'-bis(bromomethyl)-1,1'-binaphthyl, subsequent reaction with an alkyl diphenylphosphinite and subsequent reduction of the bisphosphine oxide formed by means of an organodichlorosilane. This process has a number of fundamental disadvantages: to introduce the phosphorus groups into the target molecules, the latter firstly have to be brominated, and the bromine atoms are then replaced by phosphorus groups. This requires the use of expensive and toxic bromination reagents and results in the formation of superstoichiometric amounts of bromide waste. The bromination of the starting compounds generally leads to product mixtures whose handling is problematical since the arylalkyl bromides formed are lacrymatory substances which are hazardous to health. In addition, the reaction with alkyl diphenylphosphinites leads to the phosphine oxide which has to be reduced in a further step. Starting out from 2,2'-dimethylbinaphthyls, 4 steps are thus necessary to obtain the desired ligands.

Similar syntheses or partial syntheses having the same and sometimes further disadvantages are also described in the literature (M. E. Jung et al., Tetrahedron Lett. 1988, 29, 6199; H. J. Bestmann et al., Chem. Ber. 1974, 2926; T. Hayashi et al., J. Am. Chem. Soc. 1988, 110, 8153).

In EP 0 704 449, unsymmetrically substituted bis(diarylphosphinoalkyl)-1,1'-binaphthyls are prepared from 2,2'-bis(bromomethyl)-1,1'-binaphthyl via corresponding phosphonium salts. This process has the abovementioned disadvantages and is not advantageous for the preparation of symmetrical bis(diarylphosphinoalkyl)-1,1'-binaphthyls since the phosphorus groups have to be introduced into the target molecule in two steps and large amounts of salt waste are formed.

SUMMARY OF THE INVENTION

For the above reasons, there is a need to develop a new process for preparing bis(diarylphosphinoalkyl)-1,1'-binaphthyls which does not have the abovementioned disadvantages, can be carried out simply and safely and makes it possible to obtain the desired product in a high yield and purity.

This object is achieved by a process for preparing diphosphines of the formula I $$R^1R^2P-H_2C-Ar-CH_2PR^1R^2 \quad (I)$$

which comprises a) reacting dimethyl compounds of the formula II, $$H_3C-Ar-CH_3 \quad (II)$$

with a base and an N-substituted aminophosphorus halide to form bis(aminophosphinomethyl) compounds of the formula III $$R^3R^4P-H_2C-Ar-CH_2-PR^3R^4, \quad (III)$$

b) reacting the compounds of the formula III obtained in this way with HCl to form bis(dichlorophosphinomethyl) compounds of the formula IV $$Cl_2P-H_2C-Ar-CH_2-PCl_2 \quad (IV)$$

and c) reacting the compounds of the formula IV obtained in this way with organometallic reagents to give the target compounds of the formula I, where $R^1$ and $R^2$ are each, independently of one another, a substituted or unsubstituted aromatic, heteroaromatic or aliphatic hydrocarbon radical and may have a covalent bond connecting them and Ar is a substituted or unsubstituted aromatic or heteroaromatic hydrocarbon radical and $R^3$ and $R^4$ are each, independently of one another, an N-substituted alkylamino or arylamino radical.

DETAILED DESCRIPTION OF THE PREFERRED EMBODIMENTS

The process of the invention is of particular interest since the routes described in the past for obtaining the ligands of the formula I were always via benzyl halide intermediates. The process of the invention enables diphosphines to be obtained in good yields and high purities directly from the compounds of the formula II.

Bases which can be used for the reaction of compounds of the formula II in process step a) are any bases which can deprotonate benzylic $CH_3$ groups. Typical examples of such bases are alkyllithium and aryllithium compounds such as butyllithium and methyllithium, alkali metal hydrides or alkaline earth metal hydrides such as sodium hydride and potassium hydride, alkali metals or alkaline earth metals such as sodium or potassium in liquid ammonia, and also alkali metal or alkaline earth metal hydroxides or alkali metal or alkaline earth metal alkoxides, for example potassium tert-butoxide.

The process of the invention for preparing diphosphines can be illustrated by way of example by the following reaction scheme for the synthesis of 2,2'-bis(diarylphosphinomethyl)-1,1'-binaphthyls:

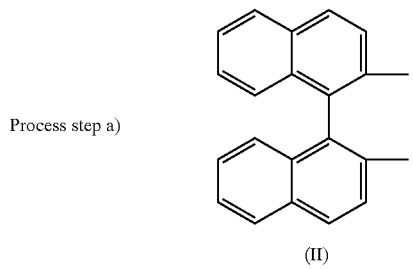
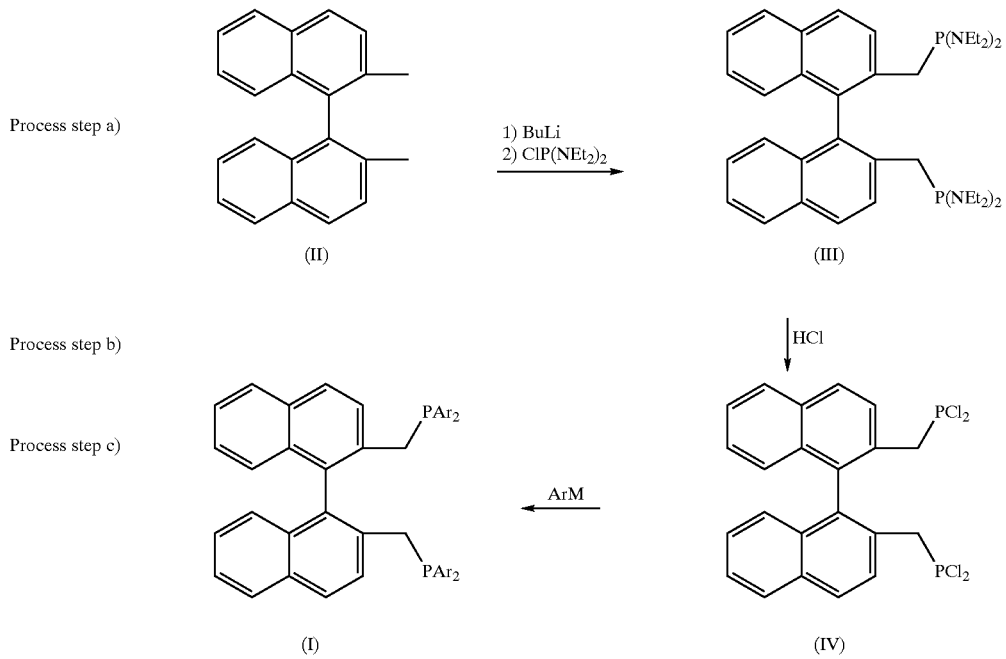

As N-substituted aminophosphorus halides in process step a), it is possible to use alkylaminophosphorus or arylaminophosphorus chlorides, bromides or iodides, where alkyl is a hydrocarbon radical selected from the group consisting of methyl, ethyl, propyl, isopropyl, butyl, isobutyl, hexyl, 2-ethylhexyl, octyl, isooctyl, nonyl or isononyl radicals and/or these radicals can have a covalent bond between them and/or alkylamino is an aliphatic heterocyclic radical having from one to 6 carbon atoms and/or aryl is an aromatic radical having from one to 14 carbon atoms, where these radicals may bear up to seven substituents selected from the group consisting of $(C_1-C_8)$-alkyl, O-alkyl-$(C_1-C_8)$, O-phenyl, phenyl, fluorine, chlorine, CN, COOH, CHO, $SO_3H$, $SO_2$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2$$(C_1-C_4)$, $PO_3H_2$, PO(O-alkyl-$(C_1-C_6)$)$_2$, $SO_3$-alkyl-$(C_1-C_4)$.

An alkylamino radical can be an aliphatic heterocyclic radical such as piperidine or pyrrole and/or an aryl radical can be an aromatic radical such as phenyl, naphthyl or benzyl. Preference is given to using bis(dialkylamino)phosphorous chlorides. For all compounds, the N—P bond has to be able to be cleaved by means of acid.

MORE DETAILED DESCRIPTION OF THE FORMULA I

The radicals $R^1$ and $R^2$ can be identical or different and can be aromatics having up to 14 carbon atoms and be able to bear up to eight substituents selected from the group consisting of $(C_1-C_8)$-alkyl, O-alkyl-$(C_1-C_8)$, O-phenyl, phenyl, fluorine, chlorine, CN, COOH, CHO, $SO_3H$, $SO_2$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2$-$(C_1-C_4)$, $PO_3H_2$, PO—(O-alkyl-$(C_1-C_6)$)$_2$, $SO_3$-alkyl-$(C_1-C_4)$.

Furthermore, the radicals $R^1$ and $R^2$ can be identical or different and be heteroaromatics having a five-, six- or seven-membered ring and nitrogen, oxygen or sulfur atoms in the ring, where further aromatic, heteroaromatic and/or aliphatic rings may be fused onto the ring and the rings may bear up to seven substituents selected from the group consisting of $(C_1-C_8)$-alkyl, O-alkyl-$(C_1-C_8)$, O-phenyl, phenyl, fluorine, chlorine, CN, COOH, CHO, $SO_3H$, $SO_3$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2$-$(C_1-C_4)$, $PO_3H_2$, PO—(O-alkyl-$(C_1-C_6)$)$_2$, $SO_3$-alkyl-$(C_1-C_4)$.

In addition, the hydrocarbon radicals $R^1$ and $R^2$ can be identical or different and be cyclic or acyclic alkyl radicals which contain up to 10 carbon atoms and may bear up to seven substituents selected from the group consisting of $(C_1-C_8)$-alkyl, O-alkyl-$(C_1-C_8)$, O-phenyl, phenyl, fluorine, chlorine, CN, COOH, CHO, $SO_3H$, $SO_2$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2$-$(C_1-C_4)$, $PO_3H_2$, PO—(O-alkyl-$(C_1-C_6)$)$_2$, $SO_3$-alkyl-$(C_1-C_4)$.

In these cases, the radicals $R^1$ and $R^2$ can also be joined by one or more covalent bonds and thus form, for example, a biphenyl, naphthyl or other cyclic system.

Ar can be a phenyl, naphthyl, anthracenyl or phenanthrenyl radical, a 1,1'-biphenyl unit or a 1,1'-binaphthyl unit, which may each bear up to eight further substituents selected from the group consisting of $(C_1-C_8)$-alkyl, O-alkyl-$(C_1-C_8)$, O-phenyl, phenyl, fluorine, chlorine, CN, COOH, CHO, $SO_3H$, $SO_2$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2$-$(C_1-C_4)$, $PO_3H_2$, PO—(O-alkyl-$(C_1-C_6)$)$_2$, $SO_3$-alkyl-$(C_1-C_4)$ or one or more fused-on benzene rings.

As an alternative, Ar can be a heteroaromatic comprising a five-, six- or seven-membered ring having nitrogen, oxygen or sulfur atoms in the ring, where further aromatic, heteroaromatic and/or aliphatic rings may be fused onto the ring and the rings may bear up to six substituents selected from the group consisting of $(C_1-C_8)$-alkyl, O-alkyl-$(C_1-C_8)$, O-phenyl, phenyl, fluorine, chlorine, CN, COOH, CHO, $SO_3H$, $SO_2$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2$-$(C_1-C_4)$, $PO_3H_2$, PO—(O-alkyl-$(C_1-C_6)$)$_2$, $SO_3$-alkyl-$(C_1-C_4)$.

Organometallic reagents used for converting compounds of the formula IV into the target compounds of the formula I in process step c) are transition metal arenes or aliphatic or aromatic alkali metal or alkaline earth metal compounds. Preference is given to using aliphatic or aromatic Grignard reagents, alkylzinc or arylzinc reagents, alkyllithium or aryllithium reagents and/or arylcopper compounds. The organometallic reagents are generally prepared separately prior to the reaction, but they can also be prepared in situ in the reaction.

Solvents used in the individual process steps a), b) and c) of the process of the invention are inert organic solvents. Without making any claim as to completeness, examples which may be mentioned are polar aprotic solvents, aliphatic ethers, aromatic or aliphatic hydrocarbons, aromatic and aliphatic halogenated hydrocarbons, alcohols, esters, amides and mixtures thereof. Naturally, the solvents must not undergo any chemical reactions with the reactants.

The process steps a), b) and c) are preferably carried out at temperatures of from −80 to 200° C.; in most cases, it has been found to be useful to employ temperatures of from −30 to 180° C., particularly preferably from −20 to 160° C.

The particular advantage of the process of the invention is that no toxic benzyl and alkyl bromides are prepared and that no reduction of phosphine oxides has to be carried out.

Owing to the stability of the intermediates of the formulae III and IV, it is possible to purify these intermediates by simple crystallization so that complicated purification methods such as chromatography are not necessary. The compounds of the intermediate IV has made it possible for many new ligands which are of interest in catalysis to be obtained in a simple manner. For producing a ligand library of the ligands prepared according to the invention, the process of the invention is considerably more convenient than previously known processes.

The diphosphines prepared according to the invention can be used as ligands in metal-catalyzed reactions, in particular hydroformylations of olefins in the presence of rhodium catalysts. Preferred olefins are octenes and butenes, in particular those having high degrees of branching and/or internal double bonds.

The use of diphosphines as ligands in hydroformylation reactions is known. Thus, U.S. Pat. No. 4,694,109 describes diphosphine ligands having a BISBI structure which are used, inter alia, in the hydroformylation of olefins having internal double bonds without discussing the selectivity to the product and the activity of the catalyst.

In *Angew. Chem. Int. Ed.* 1999, 38, 336–338, L. A. van der Veen, P. C. J. Kamer and P. W. N. M. van Leeuwen report modified XANTPHOS ligands which convert 2-octene into n-nonanal at an n/i ratio of 9:1 and a turnover frequency (=TOF) of 112h$^{-1}$. The TOF is defined as the ratio of mole of aldehyde to mole of rhodium per h after a 20–30% conversion.

EP 0 653 432 describes the preparation of diphosphines analogous to NAPHOS, some of which contain fluorine-containing substituents. These ligands can be used in the hydroformylation of olefins. Here too, nothing is said about the selectivity and activity of the catalyst.

The ligands prepared according to the invention, in particular the fluorine-containing ligands analogous to NAPHOS, in metal complexes are surprisingly highly selective and active catalysts which display the highest activity known hitherto in the selective hydroformylation of olefins having internal double bonds to form the terminal aldehydes. Table 1 in the examples gives an overview.

The invention likewise provides a process for the hydroformylation of olefins having from 3 to 16 carbon atoms in the presence of rhodium catalysts, wherein the ligands used for the rhodium are diphosphines of the formula

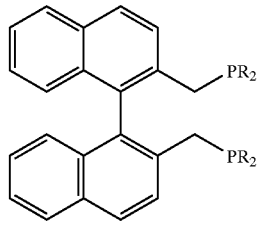

where
R=3,5-$C_6H_3F_2$; —$C_6F_5$; 2,4,5-$C_6H_2F_3$, 3,5-$C_6H_3(CF_3)_2$; 3,5-$C_6H_3(CH_3)_2$ or 3,4,5-$C_6H_2F_3$, and the n/i selectivity of the aldehydes obtained is above 85:15, preferably above 97:3.

Furthermore, turnover frequencies (TOFs), i.e. activities, of more than 150, preferably more than 300, can be achieved in the process of the present invention using the specified ligands.

The hydroformylation can be carried out in a customary manner, for example as described in J. Falbe et al "New Syntheses with Carbon Monoxide", Springer Verlag 1980, pages 93–123.

As olefins, preference is given to using those having internal double bonds, e.g. 2-butene, raffinate I or raffinate II, pentene and/or octene, in each case in isomerically pure form or as a mixture of isomers.

Raffinate I and raffinate II are $C_4$ mixtures obtained by cracking and comprise mixtures of butanes, butenes and butadienes.

EXAMPLES

The following examples illustrate the process of the invention without restricting the process to them.

1. General Procedure for Preparing the Diphosphines

Solvents: All solvents used are dried by known methods and distilled and stored under argon.

a) Preparation of 2,2'-bis[bis(diethylamino) phosphinomethyl]-1,1'-binaphthyl

The major part of the solvent is removed from 33.2 ml of n-BuLi solution (1.6 M in hexane, 53 mmol) under reduced pressure with gentle warming. After cooling in an ice bath, 25 ml of ether and 7.9 ml of tetramethylethylenediamine (53 mmol) are added. A solution of 5 g of 2,2'-dimethyl-1,1'-binaphthyl (17.7 mmol) in 30 ml of ether is slowly added dropwise while stirring and cooling. The reaction mixture is allowed to stand for 24 hours at room temperature and subsequently for a few hours at 0° C. The supernatant solution is decanted off and the precipitate obtained is washed twice with 25 ml each time of hexane.

The deep red precipitate is admixed with 50 ml of n-hexane and cooled to −70° C. A mixture of 7.5 ml of chlorobis(diethylamino)phosphine (35.4 mmol) and 25 ml of absolute n-hexane is added dropwise to the stirred suspension. After the mixture has been allowed to warm slowly to room temperature, it is stirred for another 12 hours. The solution is filtered and the precipitate is extracted twice with 50 ml of toluene. The combined filtrates are freed of solvents and of excess chlorobis(diethylamino)phosphine under reduced pressure (10$^{-3}$ torr) with warming to 80° C. The residue comprises the target product in good purity and can be used without further purification for the further reactions, e.g. to form 2,2'-bis[(dichlorophosphino)methyl]-1,1'-binaphthyl.

M=514.59 g/mol $^{31}$P-NMR (δ[ppm], C$_6$D$_6$): 88.4

$^1$H-NMR (δ[ppm], J[Hz], C$_6$D$_6$): 0.45 t(=triplet), J=7 (6H); 0.55 t, J=7 (6H); 2.5 q (=quartet), J=7 (4H); 2.6 q, J=7 (4H); 2.85 d (=doublet), J=3 (4H); 6.7–7.0 m (=multiplet) (6H); 7.6 d, J=8 (2H); 7.7–7.8 m (4H).

b) Preparation of 2,2'-bis[(dichlorophosphino)methyl]-1,1'-binaphthyl

The 2,2'-bis[bis(diethylamino)phosphinomethyl]-1,1'-binaphthyl present in the residue from the reaction described under 1a) (see above) is taken up in 150 ml of hexane. While stirring and cooling in an ice bath, gaseous HCl is passed in until the mixture is saturated (about 1 h). The mixture is filtered and the residue is washed twice with 25 ml of hexane. The combined filtrates are evaporated to about 50 ml. At −30° C., 2.9 g of 2,2'-bis[(dichlorophosphino)methyl]-1,1'-binaphthyl crystallize out.

M=484.12 g/mol

Yield: 2.9 g (44% yield based on the 2,2'-dimethyl-1,1'-binaphthyl used in 1a))

$^{31}$P-NMR (δ[ppm], J[Hz], CDCl$_3$): 180.00

$^1$H-NMR (δ[ppm], J[Hz], CDCl$_3$): 3.4–3.6 m (4H); 7.0 d, J=8.5 (2H); 7.2 m (2H); 7.43 m (2H); 7.6 d, J=8.5 (2H); 7.86 d, J=8.3 (2H); 7.94 d, J=8.5 (2H)

$^{13}$C-NMR (δ[ppm], J[Hz], CDCl$_3$): 50.3 d, $^1J_{PC}$=45.8 (P—$\underline{C}$H$_2$); 126.4 d, J=5.7; 126.5 d, J=6.7; 126.9 s; 128.1 s; 128.4 d, J=2.9; 129.0 s; 129.6 d, J=5; 133.0 d, J=16.2; 135.0 d, J=2; 135.6 s.

c) General Procedure for the Synthesis of Ligands of the Formula (I)

302 mg (12.4 mmol) of elemental magnesium are mixed with 10 ml of absolute diethyl ether under argon in a 100 ml three-necked flask provided with a magnetic stirrer. At room temperature, 12.4 mmol of the appropriately substituted bromine compound (dissolved in 10 ml of diethyl ether) are slowly (over a period of about one hour) added dropwise by means of a dropping funnel to this mixture. If the Grignard reaction does not start, a drop of 1,2-dibromoethane is added to the reaction solution. When the Grignard reaction is complete (complete reaction of the magnesium) after about 1 hour, this solution is transferred to a dropping funnel.

1.5 g (3.1 mmol) of 2,2'-bis[(dichlorophosphino)methyl]-1,1'-binaphthyl are dissolved in 25 ml of absolute THF under argon in a 150 ml three-necked flask.

At room temperature, the Grignard solution is slowly (over a period of half an hour) added dropwise to the solution of the 2,2'-bis[(dichloro-phosphino)methyl]-1,1'-binaphthyl.

The solution is subsequently heated to boiling and stirred for another two hours to complete the reaction. The solution is subsequently evaporated to dryness under argon on a rotary evaporator. The residue is dissolved in 50 ml of absolute and/or degassed toluene and admixed with 20 ml of degassed water. The mixture is stirred for half an hour. The aqueous phase is separated off and the organic phase is dried over sodium sulfate.

The sodium sulfate is subsequently filtered off, washed with 25 ml of toluene and the organic phase is evaporated to dryness under reduced pressure. The residue is recrystallized from acetone/EtOH, acetone/MeOH or toluene/hexane, or purified under argon by column chromatography on a 40 cm column (kieselguhr G 60) using absolute toluene as eluant.

The following ligands were prepared by the process of the invention.

2.) Examples of Ligands Prepared According to 1c)

a) 2,2'-Bis[bis(2,3,4,5,6-pentafluorophenyl)phosphinomethyl]-1,1'-binaphthyl 2. a)

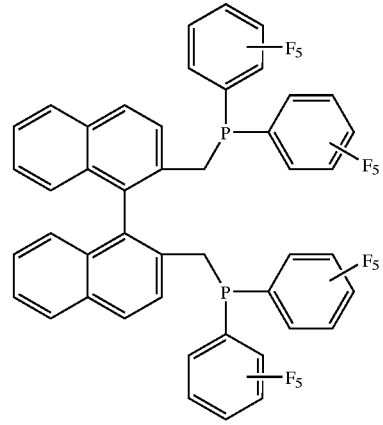

M=1010.54 g/mol

Yield: 2.3 g (73.4% of theory)

$^{31}$P-NMR (δ[ppm], J[Hz], CDCl$_3$): −46.3 qui (=quintet), $^3J_{PF}$=11

$^1$H-NMR (δ[ppm], J[Hz], CDCl$_3$): 3.6 d, J=13.8 (2H); 4.1 d, J=13.8 (2H); 6.3 d, J=8.4 (2H); 6.85 t, J=17; 7.25 t, J=10.8 (2H); 7.65 d, J=8.6 (2H); 7.7 d, J=8.1 (2H); 7.94 d, J=8.6 (2H).

b) 2,2'-Bis[bis(3,5-difluorophenyl)phosphinomethyl]-1,1'-binaphthyl 2. b)

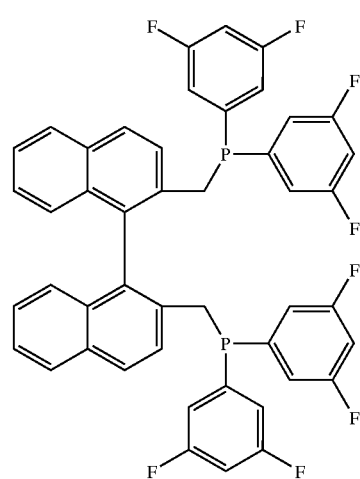

M=794.66 g/mol

Yield: 2.05 g (83.2% of theory)

$^{31}$P-NMR (δ[ppm], J[Hz], CDCl$_3$): −8.99

$^1$H-NMR (δ[ppm], J[Hz], CDCl$_3$): 3.05–3.1 m, (4H); 6.3 tt (=triplet of triplets), J=6, J=2.2 (4H); 6.53 tt, J=8.9, J=2.2 (2H); 6.65 m, (6H); 6.88 d, J=8.5 (2H); 7.1 tt, J=7, J=1 (2H); 7.2 d, J=8.5 (2H); 7.31 t, J=7.1 (2H); 7.78 t, J=8.5 (4H).

c) 2,2'-Bis[bis(2,4,5-trifluorophenyl)phosphinomethyl]-1,1'-binaphthyl

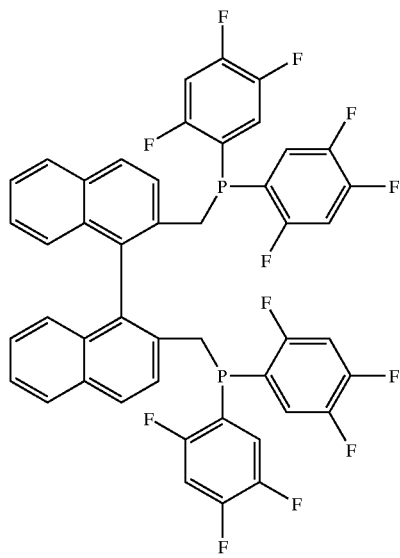

M=866.62 g/mol
Yield: 1.3 g (48.4% of theory)
$^{31}$P-NMR (δ[ppm], J[Hz], CDCl$_3$): −28.8 d, J=23.6; −29.1 d, J=25.0
$^1$H-NMR (δ[ppm], J[Hz], CDCl$_3$): 3.26 d, J$_{HH}$=14.1 (2H); 3.45 dd, J$_{HH}$=14, $^2$J$_{PH}$=3.2 (2H); 6.33 m (2H); 6.55 d; 8.7 m (2H); 6.6–6.8 m (6H); 6.92 td (=triplet of doublets), J=6.9, J=1.2 (2H); 7.26 t, J=7.4 (2H); 7.43 dd, J=8.5, J=2.2 (2H); 7.7 d (J=8.1 (2H); 7.76 d, J=7.7 (2H).

d) 2,2'-Bis[bis(3,5-dimethylphenyl)phosphinomethyl]-1,1'-binaphthyl

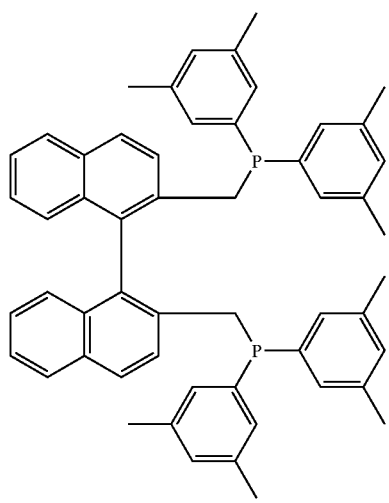

M=762.95 g/mol
Yield: 1.9 g (80% of theory)
$^{31}$P-NMR (δ[ppm], J[Hz], CDCl$_3$): −11.4
$^1$H-NMR (δ[ppm], J[Hz], CDCl$_3$): 2.1 s, 2.2 s, 2.3 s (24H); 3.1 dd, J$_{HH}$=14.2, J=2.5 (2H); 3.3 dd, J$_{HH}$=14.2, $^2$J$_{PH}$=2.2 (2H); 6.6 d, J=7.5 (4H); 6.9 m (6H), 7.1–7.2 m (6H); 7.35 dd, J=8.5, J=2 (2H); 7.4 t, J=7 (2H); 7.8 d, J=8.5 (2H); 7.85 d, J=7.9 2H).

e) 2,2'-Bis[bis(3,4,5-trifluorophenyl)phosphinomethyl]-1,1'-binaphthyl

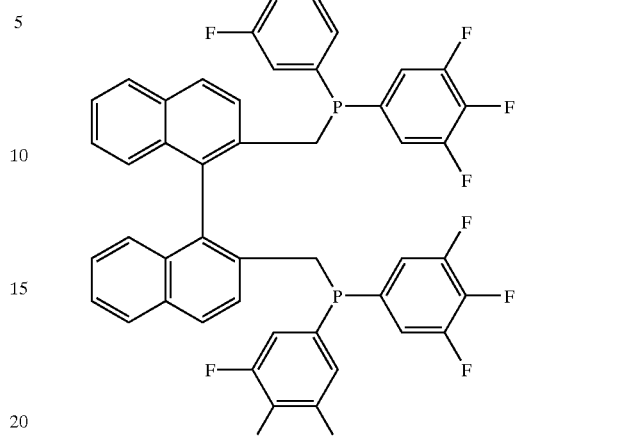

M=866.62 g/mol
Yield: 2.3 g (85% of theory)
$^{31}$P-NMR (δ[ppm], J[Hz], CDCl$_3$): −8.5
$^1$H-NMR (δ[ppm], J[Hz], CDCl$_3$): 3.1 m, (2H); 3.05 dd, J$_{HH}$=13.8, $^2$J$_{PH}$=2.7 (2H); 6.3 q, J=6.7 (4H); 6.7 m (6H); 7.05 td, J=6.7, J=1.3 (2H); 7.3 m (4H); 7.8 t, J=8.9 (4H).

f) 2,2'-Bis{bis[3,5-bis(trifluoromethyl)phenyl] phosphinomethyl}-1,1'-binaphthyl

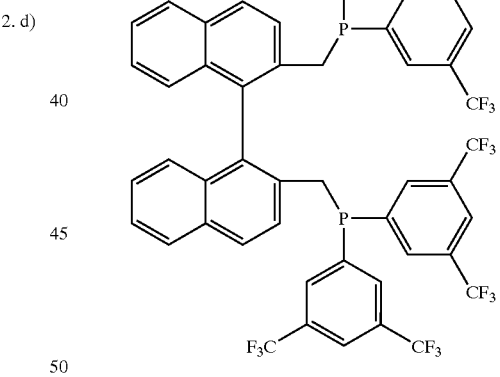

M=1126.72 g/mol
Yield: 3.1 g (88.7% of theory)
$^{31}$P-NMR (δ[ppm], J[Hz], CDCl$_3$): −10.5
$^1$H-NMR (δ[ppm], J[Hz], CDCl$_3$): 3.2 m, (4H); 6.95 d, J=8.5 (2H); 7.05–7.15 m, (4H); 7.25 d, J=4.7 (4H); 7.33 t, J=7.3 (2H); 7.47 d, J=4.5 (4H); 7.65 s, (2H); 7.7 d, J=11.1 (2H); 7.8 d, J=16.5 (4H).

3. Description of the Hydroformylation

The hydroformylation experiments were carried out either in a 100 ml autoclave (Parr Co.) provided with a magnetically driven propeller stirrer or in a 160 ml autoclave (Parr Co.) provided with a magnetic stirrer.

The hydroformylation procedure is described below by way of example for the autoclave experiment No. 1 (see table 1):

isooctane (2 ml as internal standard) and 1-pentene (8 ml, 73.0 mmol) are added to a solution of 1.88 mg of Rh(CO)$_2$acac (7.3 µmol) and 44 mg of ligand 2.f) (M: 1127, 36.5 µmol) in anisole (30 ml). After the mixture has been transferred to the autoclave, the autoclave is brought to 5 bar by means of synthesis gas (CO:H$_2$= 1:1). The autoclave is then firstly heated to 120° C. to allow the pressure to increase slowly and the pressure is subsequently adjusted to 10 bar. After 16 hours, the autoclave is switched off automatically, cooled in an ice bath and depressurized to atmospheric pressure. A GC sample is taken directly from the autoclave and measured.

TABLE 1

Rhodium-catalyzed hydroformylation in the presence of the ligands prepared according to the invention

| No. | Ligand | Olefin | T (° C.) | Yield (%) | n/i | TOF |
|---|---|---|---|---|---|---|
| 1 | 2f | 1-pentene | 120 | 82 | 96:4 | 512 |
| 2 | 2f | 2-pentene | 120 | 68 | 91:9 | 425 |
| 3 | 2f | 2-pentene | 100 | 52 | 89:11 | 325 |
| 4 | 2f | 2-butene | 120 | 66 | 91:9 | 825 |
| 5 | 2f | 2-octene | 120 | 51 | 86:14 | 319 |
| 6 | 2b | 1-pentene | 120 | 78 | 97:3 | 488 |
| 7 | 2b | 2-pentene | 120 | 59 | 94:6 | 369 |
| 8 | 2b | 2-pentene | 100 | 21 | 95:5 | 131 |
| 9 | 2e | 1-pentene | 120 | 83 | 97:3 | 519 |
| 10 | 2e | 2-pentene | 120 | 61 | 93:7 | 381 |
| 11 | 2e | 2-pentene | 100 | 24 | 94:6 | 150 |
| 12 | 2e | 2-butene | 120 | 74 | 95:5 | 925 |
| 13 | 2e | 2-octene | 120 | 48 | 91:9 | 300 |
| 14 | 2e | 4-octene | 120 | 14 | 66:34 | 88 |
| 15 | 2d | 1-pentene | 120 | 76 | 81:19 | 475 |
| 16 | 2d | 2-pentene | 120 | 11 | 78:22 | 69 |

A catalyst formed using NAPHOS, namely the parent molecule without fluorine-containing substituents, likewise displays high selectivities but gives low activities, as can be seen from the TOF values in the following table.

TABLE 2

Hydroformylation of 1- and 2-pentene using NAPHOS

| No. | Olefin | P (bar) | T (° C.) | Yield (%) | n/i | TOF |
|---|---|---|---|---|---|---|
| 1 | 1-pentene | 10 | 120 | 76 | 99:1 | 475 |
| 2 | 1-pentene | 50 | 120 | 88 | 97:3 | 550 |
| 3 | 2-pentene | 10 | 120 | 22 | 89:11 | 138 |
| 4 | 2-pentene | 50 | 120 | 7 | 55:45 | 44 |

What is claimed is:

1. A process for preparing diphosphines of formula I

R$^1$R$^2$P—H$_2$C—Ar—CH$_2$PR$^1$R$^2$    (I)

which comprises:
a) reacting a dim ethyl compound of formula II

H$_3$C—Ar—CH$_3$    (II)

with a base and an N-substituted aminophosphorus halide to form a bis(aminophosphinomethyl) compound of formula III R$^3$R$^4$P—H$_2$C—Ar—CH$_2$—PR$^3$R$^4$    (III)

b) reacting the compound of formula III with HCl to form a bis(dichlorophosphinomethyl) compound of formula IV Cl$_2$P—H$_2$C—Ar—CH$_2$—PCl$_2$    (IV)

and c) reacting the compound of formula IV with an organometallic reagent to give the product compound of formula I, wherein groups R$^1$ and R$^2$ are each, independently of one another, are:
(i) heteroaromatics having a five-, six- or seven-membered ring and nitrogen, oxygen or sulfur atoms in the ring, where further aromatic, heteroaromatic and/or aliphatic rings are optionally fused onto the ring and the rings optionally bear up to seven substituents selected from the group consisting of (C$_1$–C$_8$)-alkyl, O-alkyl-(C$_1$–C$_8$), O-phenyl, phenyl, fluorine, chlorine, CN, COOH, CHO, SO$_3$H, SO$_3$alkyl-(C$_1$–C$_6$), SO-alkyl-(C$_1$–C$_8$), CF$_3$, COO-alkyl-(C$_1$–C$_8$), COO-phenyl, PO-phenyl$_2$, PO-alkyl$_2$-(C$_1$–C$_4$), PO$_3$H$_2$, PO—(O-alkyl-(C$_1$–C$_6$))$_2$, SO$_3$-alkyl-(C$_1$–C$_4$);
(ii) cyclic or acyclic alkyl radicals which contain up to 10 carbon atoms and optionally bear up to seven substituents selected from the group consisting of (C$_1$–C$_8$)-alkyl, O-alkyl-(C$_1$–C$_8$), O-phenyl, phenyl, fluorine, chlorine, CN, COOH, CHO, SO$_3$H, SO$_2$-alkyl-(C$_1$–C$_6$), SO-alkyl-(C$_1$–C$_6$), CF$_3$, COO-alkyl-(C$_1$–C$_8$), COO-phenyl, PO-phenyl$_2$, PO-alkyl$_2$-(C$_1$–C$_4$), PO$_3$H$_2$, PO—(O-alkyl-(C$_1$–C$_8$))$_2$ and SO$_3$-alkyl-(C$_1$–C$_4$); or
(iii) aromatics having up to 14 carbon atoms and are able to bear up to eight substituents selected from the group consisting of (C$_1$–C$_8$)-alkyl, O-alkyl-(C$_1$–C$_8$), O-phenyl, phenyl, fluorine, chlorine, CN, COOH, CHO, SO$_3$H, SO$_2$-alkyl-(C$_1$–C$_6$), SO-alkyl-(C$_1$–C$_8$), CF$_3$, COO-alkyl-(C$_1$–C$_8$), COO-phenyl, PO-phenyl$_2$, PO-alkyl$_2$-(C$_1$–C$_4$), PO$_3$H$_2$, PO—(O-alkyl-(C$_1$–C$_6$))$_2$ and SO$_3$-alkyl-(C$_1$–C$_4$), wherein, when the aromatic group is a substituted phenyl group, the phenyl group can not be substituted by fluorine, trifluoromethyl or C$_{1-8}$-alkyl; and Ar is a substituted or unsubstituted aromatic or heteroaromatic hydrocarbon group and R$^3$ and R$^4$ are each, independently of one another, an N-substituted alkylamino or arylamino group.

2. The process as claimed in claim 1, wherein the radicals R$^1$ and R$^2$ have one or more covalent bonds between them.

3. The process as claimed in claim 1, wherein Ar is a naphthyl, anthracenyl, phenanthrenyl, 1,1'-biphenyl or 1,1'-binaphthyl, each of which optionally bears up to eight substituents selected from the group consisting of (C$_1$–C$_8$)-alkyl, O-alkyl-(C$_1$–C$_8$), O-phenyl, phenyl, fluorine, chlorine, CN, COOH, CHO, SO$_3$H, SO$_2$-alkyl-(C$_1$–C$_6$), SO-alkyl-(C$_1$–C$_6$), CF$_3$, COO-alkyl-(C$_1$–C$_8$), COO-phenyl, PO-phenyl$_2$, PO-alkyl$_2$-(C$_1$–C$_4$), PO$_3$H$_2$, PO—(O-alkyl-(C$_1$–C$_6$))$_2$, SO$_3$-alkyl-(C$_1$–C$_4$) and one or more fused-on benzene rings; or phenyl or phenyl substituted with at least one group selected from the group consisting of O-alkyl-(C$_1$–C$_8$), O-phenyl, phenyl, chlorine, CN, COOH, CHO, SO$_3$H, SO$_2$-alkyl-(C$_1$–C$_6$), SO-alkyl-(C$_1$–C$_6$), COO-alkyl-(C$_1$–C$_8$), COO-phenyl, PO-phenyl$_2$, PO-alkyl$_2$-(C$_1$–C$_4$), PO$_3$H$_2$, PO—(O-alkyl-(C$_1$–C$_6$))$_2$, SO$_3$-alkyl-(C$_1$–C$_4$) and one or more fused-on benzene rings.

4. The process as claimed in claim 1, wherein Ar is a heteroaromatic comprising a five-, six- or seven-membered ring having nitrogen, oxygen or sulfur atoms in the ring, where additional aromatic, heteroaromatic and/or aliphatic rings optionally are fused onto the ring and the rings optionally bear up to six substituents selected from the group consisting of (C$_1$–C$_8$)-alkyl, O-alkyl-(C$_1$–C$_8$), O-phenyl, phenyl, fluorine, chlorine, CN, COOH, CHO, SO$_3$H, SO$_2$-alkyl-(C$_1$–C$_6$), SO-alkyl-(C$_1$–C$_6$), CF$_3$, COO-alkyl-(C$_1$–C$_8$), COO-phenyl, PO-phenyl$_2$, PO-alkyl$_2$-(C$_1$–C$_4$), PO$_3$H$_2$, PO—(O-alkyl-(C$_1$–C$_6$))$_2$ and SO$_3$-alkyl-(C$_1$–C$_4$).

5. The process as claimed in claim 1, wherein said base of step a) is an alkyllithium or aryllithium compound, an alkali metal hydride or an alkaline earth metal hydride, an alkali metal or an alkaline earth metal in liquid ammonia, an alkali metal hydroxide or an alkaline earth metal hydroxide or an alkali metal alkoxide or an alkaline earth metal alkoxide.

6. The process as claimed in claim 1, wherein said N-substituted aminophosphorus halide in process step a) is alkylaminophosphorus or arylaminophosphorus chlorides, bromides or iodides, where alkyl is a hydrocarbon radical selected from the group consisting of methyl, ethyl, propyl, isopropyl, butyl, isobutyl, hexyl, 2-ethylhexyl, octyl, isooctyl, nonyl or isononyl radicals and/or these radicals optionally have a covalent bond between them and/or alkylamino is an aliphatic heterocyclic radical having from one to 6 carbon atoms and/or aryl is an aromatic radical having from one to 14 carbon atoms, where these radicals optionally bear up to seven substituents selected from the group consisting of $(C_1-C_8)$-alkyl, O-alkyl-$(C_1-C_8)$, O-phenyl, phenyl, fluorine, chlorine, CN, COOK CHO, $SO_3H$, $SO_2$-alkyl-$(C_1-C_6)$, SO-alkyl-$(C_1-C_6)$, $CF_3$, COO-alkyl-$(C_1-C_8)$, COO-phenyl, PO-phenyl$_2$, PO-alkyl$_2(C_1-C_4)$, $PO_3H_2$, PO(O-alkyl-$(C_1-C_6))_2$ and $SO_3$-alkyl-$(C_1-C_4)$, wherein, when the aromatic group is a substituted phenyl group, the phenyl group can not be substituted by fluorine, trifluoromethyl or $C_{1-8}$-alkyl.

7. The process as claimed in claim 1, wherein said organometallic reagent in process step c) is a transition metal arene, an aliphatic or aromatic alkali metal compound or an alkaline earth metal compound, an aliphatic or aromatic Grignard reagent, an alkylzinc or arylzinc reagent, an alkyllithium or aryllithium reagent, an arylcopper compound or a mixture thereof.

* * * * *